United States Patent
Thiebaut et al.

(12) 
(10) Patent No.: US 11,116,301 B2
(45) Date of Patent: Sep. 14, 2021

(54) DEVICE FOR TREATING HUMAN KERATIN MATERIALS

(71) Applicants: L'OREAL, Paris (FR); SEB S.A., Ecully (FR)

(72) Inventors: Laure Thiebaut, Chlichy (FR); Franck Mandica, Francheville (FR); Hélène Pernot, Lyons (FR); Johan Sabattier, Mornant (FR)

(73) Assignee: L'OREAL, Paris (FR)

( * ) Notice: Subject to any disclaimer, the term of this patent is extended or adjusted under 35 U.S.C. 154(b) by 298 days.

(21) Appl. No.: 16/062,924

(22) PCT Filed: Dec. 6, 2016

(86) PCT No.: PCT/EP2016/079922
§ 371 (c)(1),
(2) Date: Jun. 15, 2018

(87) PCT Pub. No.: WO2017/102451
PCT Pub. Date: Jun. 22, 2017

(65) Prior Publication Data
US 2018/0368550 A1     Dec. 27, 2018

(30) Foreign Application Priority Data

Dec. 17, 2015   (FR) .................................... 1562645

(51) Int. Cl.
*A45D 34/00*     (2006.01)
*A45D 34/04*     (2006.01)
(Continued)

(52) U.S. Cl.
CPC ........... *A45D 34/04* (2013.01); *A61N 1/0428* (2013.01); *A61N 1/30* (2013.01); *A45D 34/041* (2013.01);
(Continued)

(58) Field of Classification Search
CPC ...... A61N 1/0428; A61N 1/0448; A61N 1/26; A61N 1/322; A61H 2015/0007;
(Continued)

(56) References Cited

U.S. PATENT DOCUMENTS

| | | |
|---|---|---|
| 4,858,600 A | 8/1989 | Gross et al. |
| 5,090,402 A | 2/1992 | Bazin et al. |

(Continued)

FOREIGN PATENT DOCUMENTS

| | | |
|---|---|---|
| CN | 1313213 C | 5/2007 |
| CN | 101020513 A | 8/2007 |

(Continued)

OTHER PUBLICATIONS

Japanese Office Action for JP2018-531659 dated Jun. 21, 2019 with English Translation (10 pages).

(Continued)

*Primary Examiner* — Nathan R Price
*Assistant Examiner* — Tania Ismail
(74) *Attorney, Agent, or Firm* — Shumaker, Loop & Kendrick, LLP

(57) ABSTRACT

A device for treating human keratin materials that delivers a cosmetic or dermatological composition onto the latter together with the application of an electric current, in particular an electrophoresis device, the composition applied being contained in a cartridge carried by the device, the cartridge having a body that forms a reservoir and a piston through which a drive screw passes and which can move in the body under the effect of the relative rotation of the screw and the piston, the device comprising an electric drive motor for bringing about this relative rotation of the screw and of the piston, and an electronic circuit for controlling the electric motor.

7 Claims, 1 Drawing Sheet

(51) Int. Cl.
  *A61N 1/04* (2006.01)
  *A61N 1/30* (2006.01)
  *A61H 15/00* (2006.01)
  *A61H 7/00* (2006.01)
  *A61N 1/26* (2006.01)
  *A61N 1/32* (2006.01)
  *A61M 35/00* (2006.01)
  *A61H 15/02* (2006.01)

(52) U.S. Cl.
  CPC .. *A45D 2034/005* (2013.01); *A45D 2200/202* (2013.01); *A61H 7/003* (2013.01); *A61H 15/0078* (2013.01); *A61H 15/0085* (2013.01); *A61H 15/02* (2013.01); *A61H 2015/005* (2013.01); *A61H 2015/0007* (2013.01); *A61H 2015/0014* (2013.01); *A61H 2015/0042* (2013.01); *A61H 2015/0064* (2013.01); *A61H 2201/10* (2013.01); *A61H 2201/105* (2013.01); *A61M 35/003* (2013.01); *A61M 2210/04* (2013.01); *A61N 1/0448* (2013.01); *A61N 1/26* (2013.01); *A61N 1/322* (2013.01)

(58) Field of Classification Search
  CPC .... A61H 2015/0014; A61H 2015/0042; A61H 2015/005; A61H 2015/0064; A61H 15/0078; A61H 15/0085; A61H 15/02; A61H 2201/10; A61H 2201/1058; A61H 2201/1267; A61H 7/003; A61M 35/003; A45D 34/04; A45D 34/041
  See application file for complete search history.

(56) References Cited

U.S. PATENT DOCUMENTS

| | | | |
|---|---|---|---|
| 5,131,384 | A | 7/1992 | Obagi |
| 6,535,761 | B2 | 3/2003 | Bernabei |
| 6,947,791 | B2 | 9/2005 | Zhang et al. |
| 7,775,735 | B2 * | 8/2010 | Habatjou ............ A61H 15/0085 401/220 |
| 2005/0107832 | A1 | 5/2005 | Bernabei |
| 2005/0209538 | A1 * | 9/2005 | Lev .................... A61H 15/0078 601/15 |
| 2006/0076361 | A1 | 4/2006 | Rueschhoff et al. |
| 2008/0200861 | A1 | 8/2008 | Shalev et al. |
| 2010/0217176 | A1 | 8/2010 | Carrara et al. |
| 2010/0274329 | A1 | 10/2010 | Bradley et al. |
| 2012/0109041 | A1 | 5/2012 | Munz |
| 2012/0121309 | A1 | 5/2012 | Liu |
| 2013/0204178 | A1 | 8/2013 | Luzon et al. |
| 2013/0264358 | A1 | 10/2013 | Fallat, II et al. |
| 2015/0190074 | A1 | 7/2015 | McRae |

FOREIGN PATENT DOCUMENTS

| | | |
|---|---|---|
| CN | 101532190 A | 9/2009 |
| CN | 203777287 U | 8/2014 |
| CN | 103249339 A | 2/2017 |
| EP | 1885217 A2 | 2/2008 |
| FR | 2619308 A1 | 2/1989 |
| FR | 2917299 A1 | 12/2008 |
| FR | 3015300 A1 | 6/2015 |
| GB | 2372705 A | 9/2002 |
| JP | S48108873 U | 12/1973 |
| JP | H01135015 U | 9/1989 |
| JP | H0271742 A | 3/1990 |
| JP | 2002369985 A | 12/2002 |
| JP | 2009-179915 A1 | 8/2009 |
| JP | 2011502656 A | 1/2011 |
| JP | 2013544282 A | 12/2013 |
| JP | 2015510419 A | 4/2015 |
| RU | 2270041 C2 | 2/2006 |
| RU | 2010123941 A | 12/2011 |
| WO | 2006130643 A2 | 5/2006 |
| WO | 2008/057640 A2 | 5/2008 |
| WO | 2010111997 A2 | 10/2010 |
| WO | 2013118114 A1 | 8/2013 |
| WO | 2014/180555 A1 | 11/2014 |
| WO | 2014180555 A1 | 11/2014 |
| WO | 2014/207750 A1 | 12/2014 |
| WO | 2015/091044 A1 | 6/2015 |
| WO | 2015091044 A1 | 6/2015 |
| WO | 2015097624 A1 | 7/2015 |

OTHER PUBLICATIONS

Japanese Office Action for JP2018-531657 dated Jul. 1, 2019 with English Translation (11 pages).
Japanese Office Action for JP2018-531653 dated Jul. 29, 2019 with English Translation (12 pages).
Japanese Office Action for JP2018-531626 dated Aug. 5, 2019 with English Translation (8 pages).
International Search Report dated Mar. 21, 2017 in International Patent Application No. PCT/EP2016/079911 (3 pages).
Written Opinion dated Mar. 21, 2017 in International Patent Application No. PCT/EP2016/079911 (5 pages).
International Preliminary Report on Patentability dated Jun. 19, 2018 in International Patent Application No. PCT/EP2016/079911 (6 pages).
International Search Report dated Mar. 21, 2017 in International Patent Application No. PCT/EP2016/079915 (3 pages).
Written Opinion dated Mar. 21, 2017 in International Patent Application No. PCT/EP2016/079915 (5 pages).
International Preliminary Report on Patentability dated Jun. 19, 2018 in International Patent Application No. PCT/EP2016/079915 (6 pages).
International Search Report dated Mar. 21, 2017 in International Patent Application No. PCT/EP2016/079923 (3 pages).
Written Opinion dated Mar. 21, 2017 in International Patent Application No. PCT/EP2016/079923 (5 pages).
International Preliminary Report on Patentability dated Jun. 19, 2018 in International Patent Application No. PCT/EP2016/079923 (6 pages).
International Search Report dated Feb. 24, 2017 in International Patent Application No. PCT/EP2016/079927 (3 pages).
Written Opinion dated Feb. 24, 2017 in International Patent Application No. PCT/EP2016/079927 (5 pages).
International Preliminary Report on Patentability dated Jun. 19, 2018 in International Patent Application No. PCT/EP2016/079927 (6 pages).
International Search Report dated Mar. 24, 2017 in International Patent Application No. PCT/EP2016/079922 (3 pages).
Written Opinion International Search Report dated Mar. 24, 2017 in International Patent Application No. PCT/EP2016/079922 (5 pages).
International Preliminary Report on Patentability dated Jun. 19, 2018 in International Patent Application No. PCT/EP2016/079922 (6 pages).
U.S. Appl. No. 16/062,875, filed Jun. 13, 2018.
U.S. Appl. No. 16/062,183, filed Jun. 14, 2018.
U.S. Appl. No. 16/062,209, filed Jun. 14, 2018.
U.S. Appl. No. 16/062,913, filed Jun. 15, 2018.
Russian Office Action of substantive examination for RU Application No. 2018121971/14 dated Mar. 18, 2019; 13 pages (includes English Translation).
Final Rejection for U.S. Appl. No. 16/062,209 dated Jun. 24, 2020 (12 pages).
Final Rejection for U.S. Appl. No. 16/062,913 dated Jun. 25, 2020 (8 pages).
Korean Office Action for Korean Pat. App. No. 10-2018-7017071 dated Jun. 20, 2020 (10 pages).
First Office Action for CN Patent App. No. 201680074289.9 with English Translation dated Jul. 3, 2020 (12 pages).
Japanese Office Action for JP2018-531627 dated Jun. 3, 2019 with English Translation (7 pages).
Non-Final Office Action in U.S. Appl. No. 16/062,183 dated Feb. 20, 2020.

(56) References Cited

OTHER PUBLICATIONS

Non-Final Office Action in U.S. Appl. No. 16/062,209 dated Feb. 20, 2020.
Non-Final Office Action in U.S. Appl. No. 16/062,913 dated Apr. 1, 2020.
Non-Final Office Action in U.S. Appl. No. 16/061,875 dated Apr. 2, 2020.
Russian Office Action of Substantive Examination for RU Application No. 2018121748/14 (034416) dated Apr. 2, 2019 with English Translation (10 pages).
Russian Office Action of Substantive Examination for RU Application No. 2018121755/14 (034427) dated Apr. 2, 2019 with English Translation (10 pages).
Russian Office Action of Substantive Examination for RU Application No. 2018121754/14 (034423) dated Apr. 2, 2019 with English Translation (8 pages).
Non-Final Rejection for U.S. Appl. No. 16/062,913, dated Dec. 31, 2020 (9 pages).
Non-Final Office Action for U.S. Appl. No. 16/061,875, dated Jan. 6, 2021 (16 pgs.).
Final Rejection for U.S. Appl. No. 16/061,875 dated Aug. 5, 2020 (12 pages).
Non-Final Office Action for U.S. Appl. No. 16/062,209 dated Nov. 9, 2020 (10 pages).
Advisory Action for U.S. Appl. No. 16/061,875 dated Nov. 9, 2020 (3 pages).
Final Rejection for U.S. Appl. No. 16/062,183 dated Aug. 13, 2020 (13 pages).
English Translation of First Office Action for Chinese Pat. Application No. 201680074631.5, dated Apr. 9, 2021 (6 pages).
Final Rejection for U.S. Appl. No. 16/061,875, dated Jun. 28, 2021 (16 pages).
Non-Final Office Action for U.S. Appl. No. 16/062,209, dated May 26, 2021 (9 pages).
Notice of Allowance for U.S. Appl. No. 16/062,913, dated May 13, 2021 (8 pages).

\* cited by examiner

DEVICE FOR TREATING HUMAN KERATIN MATERIALS

BACKGROUND

The present invention relates to devices for treating human keratin materials by applying a cosmetic or dermatological composition thereto together with the application of an electric current.

It is known that the application of an electric current to the skin can facilitate the penetration of an active agent. It is thus known to treat human keratin materials with the aid of iontophoresis devices. Iontophoresis allows the diffusion of active agents through the skin by virtue of electrical stimulation in a non-invasive manner. The current administered may be adjustable in terms of intensity and polarity (anodic or cathodic current). The transcutaneous diffusion of the molecules via iontophoresis is based on two principles, namely electrorepulsion and electroosmosis.

Electrorepulsion is the migration of an ionized molecule by repulsion of charges of the same sign. Thus, a positively charged substance will diffuse through the skin at the anode (+).

Electroosmosis is the migration of a molecule, even a non-ionized molecule, by entrainment associated with the flow of water from the anode to the cathode during iontophoresis.

US 2013/0204178 A1 discloses an iontophoresis device which comprises a product reservoir. A motor sets into rotation a shaft which axially moves a threaded element. This element presses on a piston outside the reservoir so as to reduce the volume thereof.

A drawback with such a system is its axial space requirement, since, when the reservoir is full, the entire threaded element is situated outside the reservoir. This limits the volume of the reservoir and imposes space constraints that limit possible shapes in terms of ergonomics.

Finally, each time the reservoir is changed, the threaded element has to be returned to its initial position, thereby complicating the operation of changing the reservoir.

SUMMARY

There is a need to be able to precisely meter the quantity of product dispensed by the treatment device, in order in particular to avoid an excess of composition that is likely to increase the intensity of the current through the human keratin materials, on account of the electrically conductive nature of the composition, or, by contrast, an insufficient quantity of composition, which impairs the establishment of the electric current and consequently has a detrimental effect on the proper operation of the device.

There is also a need to make it easier to replace the cartridge containing the product.

The invention aims to meet this need and achieves this by virtue of a device for treating human keratin materials that delivers a cosmetic or dermatological composition onto the latter together with the application of an electric current, the composition applied being contained in a cartridge carried by the device, the cartridge having a body that forms a reservoir and a piston through which a drive screw passes, the piston being able to move in the body under the effect of the relative rotation of the screw and the piston, the device comprising an electric drive motor for bringing about this relative rotation of the screw and of the piston, and an electronic circuit for controlling the electric motor.

By virtue of the use of a cartridge as defined above, the invention makes it possible to precisely control the movement of the piston within the body of the cartridge and, consequently, the quantity of product dispensed, and in particular to regulate the flow rate.

On account of the saving in axial space requirement compared with the device disclosed in US 2013/0204178, it is possible, given the same volume of product and axial space requirement, to have a smaller axial section of the cartridge; as a result, for an identical forward travel of the piston, the quantity dispensed is lower, making it possible to further increase precision, if desired, or, given the same precision, to make a saving in space requirement. Given the same space requirement, an increase in autonomy can be achieved.

The regularity of the composition dispensing flow rate is advantageous in an iontophoresis treatment since it makes it possible to ensure the efficacy and the stability of the micro-current applied and therefore the comfort of the user during the treatment.

The invention also makes it possible to obtain a relatively compact device that is compatible with easy replacement of the cartridge, if desired, such that it is possible to refill the device with product after the original cartridge has been used up.

In particular, the replacement of the cartridge does not make it necessary to return a threaded element to its initial position over a long path. The new cartridge fitted has a piston already in position.

The electronic circuit is preferably designed to automatically control the operation of the motor at least depending on the impedance between an electrode and a counterelectrode allowing said electric current to flow.

In a variant, the motor is controlled by the actuation of a control button by the user, allowing the user to control the quantity of product applied themselves. The actuation of the control button causes the motor to be started, for example, for a predefined time corresponding to the dispensing of a predetermined metered quantity.

If need be, the device has a user interface which signals to the user a need to apply product.

In a preferred embodiment, the cartridge comprises a head that is mounted so as to rotate relative to the body, the head being held fixedly in the device and the motor driving the body in rotation relative to the head.

It is very particularly advantageous for the device to comprise a ring gear coaxial with the body, a pinion of the motor meshing with said ring gear. This can make it possible to use a motor that is a non-geared motor or has a lower reduction ratio, and thus has a lower cost.

The body of the cartridge preferably has at least one relief, preferably a notch, for taking up torque, with which the ring gear engages.

The pinion of the motor can engage with teeth on the inside of the ring gear, making it possible to increase compactness by disposing the motor in line with the cartridge.

Preferably, the device comprises a treatment head that is removable and provides access, when removed, to a housing containing the cartridge. This removable assembly has the double advantage both of making it possible to change the cartridge easily and of making it easier to clean the treatment head, if necessary.

The treatment head may comprise massage balls which are pressed against the skin.

BRIEF DESCRIPTION OF THE DRAWINGS

The invention may be better understood from reading the following detailed description of a non-limiting implementation example thereof and from examining the appended drawing, in which.

DETAILED DESCRIPTION

Figure 1:
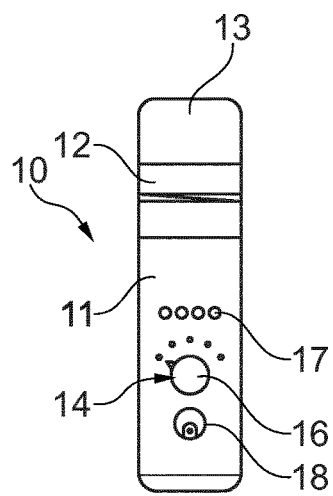
FIG. 1 schematically shows an elevation view of a treatment device according to the invention.

The treatment device 10 according to the invention, shown in FIG. 1, comprises a casing 11 which bears a treatment head 12 that can be covered by a removable protective cap 13 when not in use.

The treatment head can comprise applicator members 15 such as balls, the composition being dispensed through a gap between the applicator members and their housings.

The device 10 can comprise a user interface 14 which comprises for example a regulating button 16, one or more indicator lights 17, and an on-off switch 18.

In the example in question, the treatment device 10 is an electrophoresis device and makes it possible to subject the treated region, in particular a zone of the skin on the face or the body, to the joint action of the composition and an electric current.

The interface 14 can make it possible in particular to regulate the intensity of the electric current applied to the keratin materials treated and can also signal to the user the need to apply more composition, if need be.

Figure 2:
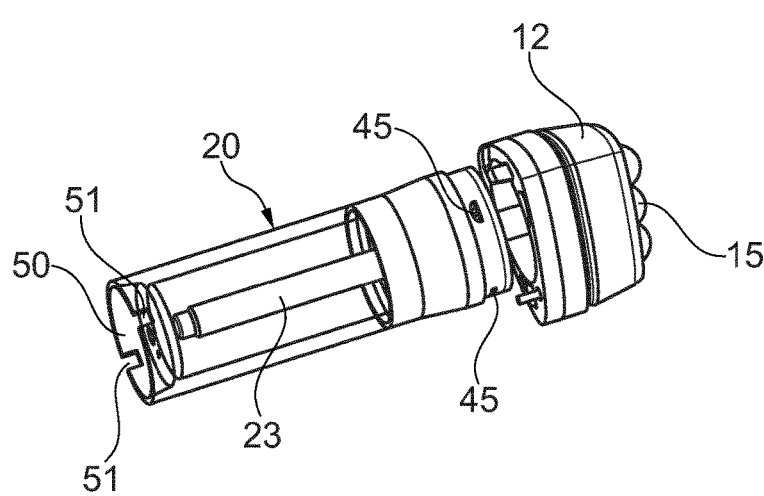
FIG. 2 shows, on its own, the cartridge containing the product, which is accommodated in the device from FIG. 1, and also the treatment head.
Figure 3:
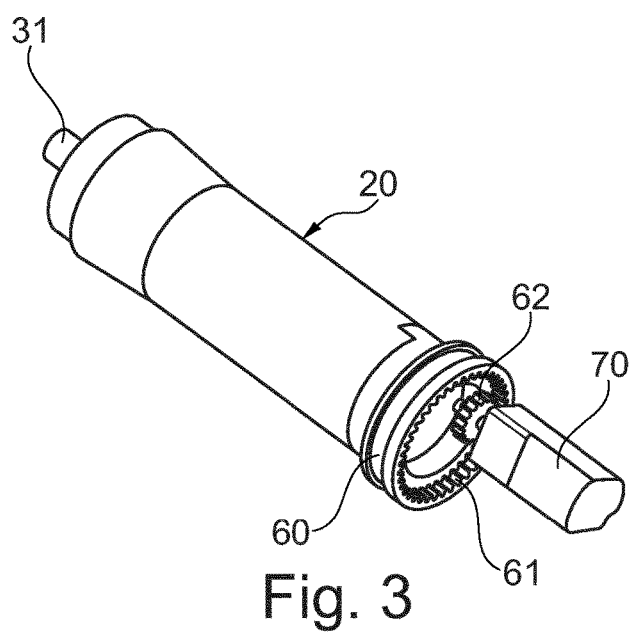
FIG. 3 shows the cartridge from FIG. 2, and also the electric drive motor.
Figure 5:
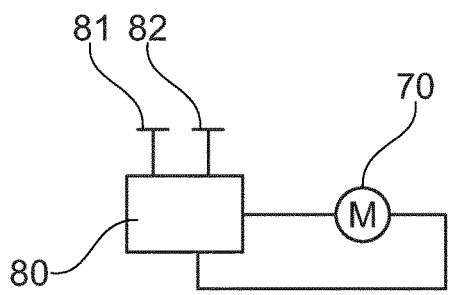
FIG. 5 is a simplified diagram of the electric circuit of the device.
Figure 4:
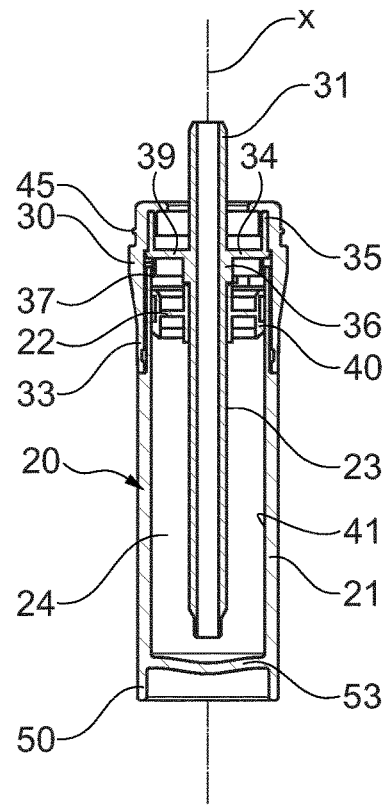
FIG. 4 shows the cartridge on its own, in longitudinal section.

The composition which is dispensed by the device 10 is contained in a cartridge 20, which can be seen in FIGS. 2 to 4, and which comprises, in the example in question, a body 21 inside which a piston 22 which is engaged with a hollow screw 23 can move.

The piston 22 can move along the longitudinal axis X of the cartridge 20 during a relative movement of the screw 23 and of the piston in rotation about the axis X. The movement of the piston 22 inside the body 21 takes place so as to reduce the volume of the reservoir 24 situated under the piston 22, the volume of this reservoir 24 being for example between 2 and 5 ml, being for example around 3 ml.

The hollow screw 23 engages with a corresponding thread on an opening passing through the piston 22.

The screw 23 defines a passage through which the product contained in the reservoir 24 can flow when the piston 22 moves in the body 21 in the direction of a reduction in volume of the reservoir 24.

The screw 23 is fixed with respect to a head 30 with respect to which the body 21 can turn, and communicates with a dispensing nozzle 31.

The head 30 comprises an external ring 33 which is held axially on the body 21 while being able to turn about the axis X relative to the latter, and a support part 34 for the screw 23 which comprises, at its periphery, a sealing skirt 35 that is pressed in a leaktight manner against the internal surface of the ring 33.

The support part 34 comprises a partition 39 which supports the skirt 35 and is connected to a portion 36 situated at the junction between the screw 23 and the nozzle 31.

The screw 23, the nozzle 31 and the support part 34 are made in one piece by moulding material.

A sealing lip 37 is pressed against the radially internal surface of the body 21, close to its upper end. This lip 37 is connected at the top to the partition 39, being moulded in one piece with the latter, just like the skirt 35.

The piston 22 has, at its periphery, a sealing skirt 40 which is pressed with friction against the internal surface 41 of the body 21.

The friction force of the piston 22 against the internal surface 41 of the body 21 is enough to prevent the latter from rotating relative to the body while the body 21 rotates, such that the relative rotation of the screw 23 and of the piston 22 causes the latter to move along the axis X. This movement is accompanied by a reduction in the volume of the reservoir 24 and by product contained in the cartridge rising up through the screw 23 and then through the nozzle 31.

The head 30 of the cartridge comprises reliefs 45 which cooperate with corresponding reliefs on the inside of the device 1 so that the head 30 is prevented from rotating inside the device when the cartridge 20 is in position thereon.

The reliefs 45 are for example in the form of bosses which are distributed at regular angular intervals around the axis X.

The head 30 of the cartridge 20 can also be prevented from rotating inside the device purely by friction, if need be.

At its end away from the head 30, the cartridge 20 has a drive skirt 50 which is advantageously provided, as can be seen in particular in FIG. 2, with diametrically opposite notches 51. The drive skirt 50 extends under the end wall 53 of the reservoir 24.

The device 10 comprises a ring gear 60 which engages with the drive skirt 50 when the cartridge 20 is in position, as illustrated in FIG. 3. This ring gear 60 comprises internal teeth 61 which mesh with the pinion 62 mounted on the shaft of an electric motor 70, which can be a geared motor or a non-geared motor. The advantage of using a ring gear 60 as illustrated, with a relatively large diameter, is that a relatively large step-down ratio is obtained between the pinion 62 and the teeth 61, making it possible to use a non-geared motor or a motor with a a low reduction ratio.

The motor 70 is powered by an electronic circuit 80, disposed inside the device 10, which is connected to the interface 14 and which controls the operation of the motor.

The electronic circuit 80 is designed to subject the keratin materials treated to an electric current and is connected to an electrode 81 and a counterelectrode 82.

The electrode 81 is for example in contact with the composition inside the device, in particular with the treatment head 12. The device thus makes use of the fact that the composition is electrically conductive, and so it is possible to avoid having to place the electrode in direct contact with the keratin materials treated.

The counterelectrode 82 is in contact with the person being treated, being for example in contact with the hand of the user holding the device 10.

The electronic circuit 80 can be designed to measure the impedance between the electrode 81 and the counterelectrode 82 and, depending on the impedance thus determined, act on the electric motor 70 so as to dispense or not dispense, or modify the flow rate of the quantity of product dispensed.

The regulating button 16 can make it possible to modify the intensity of the current which flows between the electrode 81 and the counterelectrode 82, if need be.

The motor 70 can be controlled automatically depending on the impedance measured, such that the user does not have to trigger the dispensing of the product themselves.

In a variant, the electronic circuit 80 can detect, by measuring the impedance, a need for composition between the electrode 81 and the keratin materials treated. A warning device, for example one of the indicator lights 17, can be lit to signal to the user the need to apply the composition, and the device can comprise a control button (not shown) which the user can press in order to trigger the dispensing of a new metered quantity of product. The need for composition can also be signalled in some other way than by the lighting of an indicator light, for example in a vibrating manner.

During use, the piston 22 drops in the cartridge 20 as the reservoir 24 is emptied. When the piston 22 comes into abutment against the end of the cartridge, this can be detected by the supply current of the motor 70 being measured, and a message can then be output to draw the user's attention so as to invite them to replace the cartridge 20.

Preferably, the treatment head 12 is disposed in a removable manner on the casing 11 of the device, so as to allow the user, when it is removed, to access the housing containing the cartridge 20 in order to exchange the latter.

The treatment head 12 can comprise an end piece in which the dispensing nozzle 31 fits in a leaktight manner when the head 12 is put back on the casing 11 after the cartridge has been replaced.

The invention is not limited to the example which has just been described.

In particular, the body 21 of the cartridge can be mounted fixedly in the device and the head 30 can be driven in rotation by virtue of a motor situated for example in the treatment head 12, which can mesh with a gearwheel that turns with the dispensing nozzle 31.

The invention claimed is:

1. A device for treating human keratin materials that delivers a cosmetic or dermatological composition onto the human keratin materials with an application of an electric current, the composition applied being contained in a cartridge carried by the device, the cartridge having a body that forms a reservoir and a piston through which a drive screw passes and which can move in the body under the effect of the relative rotation of the screw and the piston, the device comprising an electric drive motor for bringing about this relative rotation of the screw and of the piston, and an electronic circuit for controlling the electric motor, wherein:

the cartridge comprises a head that rotates relative to the body, the head being held fixedly in the device and the motor driving the body in rotation relative to the head, and the devices further comprising a treatment head that is removable and provides access, when removed to a housing containing the cartridge.

2. The device according to claim 1, wherein the electronic circuit is designed to control the operation of the motor at least depending on an impedance between an electrode and a counterelectrode of the device allowing said electric current to flow.

3. The device according to claim 1, which comprises a ring gear coaxial with the body, a pinion of the motor meshing with said ring gear.

4. The device according to claim 3, wherein the motor is a non-geared motor.

5. The device according to claim 3, wherein the body of the cartridge has at least one relief, for taking up torque, with which the ring gear engages.

6. The device according to claim 3, wherein the teeth of the ring gear are on the inside.

7. The device of claim 4, wherein the body of the cartridge has at least one relief, for taking up torque, with which the ring gear engages.

* * * * *